United States Patent [19]

Simon et al.

[11] Patent Number: 5,651,782
[45] Date of Patent: Jul. 29, 1997

[54] METHOD AND APPARATUS FOR IMPLANTING AN ARTIFICIAL MESHWORK IN GLAUCOMA SURGERY

[75] Inventors: Gabriel Simon; Jean-Marc Legeais; William Lee; Jean-Marie Parel, all of Miami, Fla.

[73] Assignee: University of Miami, Miami, Fla.

[21] Appl. No.: 663,404

[22] Filed: Jun. 13, 1996

Related U.S. Application Data

[62] Division of Ser. No. 253,696, Jun. 3, 1994, Pat. No. 5,573,544, which is a division of Ser. No. 34,870, Mar. 19, 1993, Pat. No. 5,342,570.

[51] Int. Cl.⁶ .................................................. A61B 19/00
[52] U.S. Cl. ............................ 606/1; 606/166; 359/833
[58] Field of Search .................................... 351/163, 159, 351/200, 212, 213, 215, 219; 359/618, 627, 615, 599, 720–727, 831–835

[56] References Cited

U.S. PATENT DOCUMENTS

| | | |
|---|---|---|
| 4,347,091 | 8/1982 | Hauck . |
| 4,402,681 | 9/1983 | Haas . |
| 4,424,335 | 1/1984 | Szycher . |
| 4,470,159 | 9/1984 | Peyman . |
| 4,617,081 | 10/1986 | Bleau . |
| 4,722,724 | 2/1988 | Schocket . |
| 4,806,382 | 2/1989 | Goldberg . |
| 4,909,799 | 3/1990 | Thulesius . |
| 4,936,825 | 6/1990 | Ungerleider . |
| 4,946,436 | 8/1990 | Smith . |
| 4,968,296 | 11/1990 | Ritch . |
| 4,969,869 | 11/1990 | Burgin . |
| 4,986,831 | 1/1991 | King . |
| 5,041,081 | 8/1991 | Odrich . |
| 5,041,133 | 8/1991 | Sayano . |
| 5,064,435 | 11/1991 | Porter . |
| 5,178,604 | 1/1993 | Baerveldt . |
| 5,190,555 | 3/1993 | Wetter . |
| 5,368,597 | 11/1994 | Pagedas . |
| 5,370,650 | 12/1994 | Tovey . |
| 5,486,188 | 1/1996 | Smith ........................... 606/166 |
| 5,496,339 | 3/1996 | Koepnick ..................... 606/166 |

FOREIGN PATENT DOCUMENTS 1718913  3/1992  U.S.S.R. .

OTHER PUBLICATIONS

Lloyd et al, Combined Molteno Implanation ... Glaucomas, Ophthalmology, 1991, pp. 1402–1405.
Rockwood et al., Glaucoma Filtering Surgery with 5-Fluorouracil, Ophthalmology, 1987, 1071–1078.
Richter, Retreatment with Argon Laser Trabeculoplasty, Ophthalmology, 1987, pp. 1085–1089.
Gross, et al, Surgical Therapy of Chronic Glaucoma ... and Pseudophakia, Ophthalmology, 1988, pp. 1195–1201.
Cameron et al, Clinico–histopathologic . . . Implant, Ophthalmology, 1988, pp. 1189–1193.
Hitchings, et al, Use of One–Piece . . . Surgery, Ophthalmology, 1987, pp. 1079–1084.
Schocket et al, Anterior Chamber Tube . . . Refractory Glaucomas, Ophthalmology, 1985, pp. 553–562.
Tomey et al, The Glaucomas in Aphakia and Pseudophakia, Survey of Opthalmology, 1991, pp. 79–112.

(List continued on next page.)

*Primary Examiner*—Glenn Dawson
*Attorney, Agent, or Firm*—Cushman Darby & Cushman Intellectual Property Group of Pillsbury Madison & Sutro, LLP

[57] ABSTRACT

A method and device which is used to insert an implant in order for treating an eye with glaucoma in order to lower the intraocular pressure of the eye. The implant is an artificial meshwork. The implant is attached to a guide knife which is inserted into the anterior chamber of the eye. The knife is then removed leaving the implant in place. During the operation, a prismatic lens with c-shaped vacuum ring is used to help assist the surgeon in viewing the anterior chamber of the eye and stabilizing the eye.

8 Claims, 13 Drawing Sheets

OTHER PUBLICATIONS

OptiMed Inc., Glaucoma Pressure Regulator, Pamphlet.

OptiMed Inc., Molteno Implant, Pamphlet.

E. Benson Hood Laboratories, Krupin Eye Valves, For Surgical Management . . . Glaucomas, Literature 1991.

Dobrogowski, A New Glaucoma Filter Implant, Ophthalmic Surgery, Jul. 1990, pp. 481–485.

Neubauer, Complications after Modern Filter Operations in Glaucoma, Dev. Ophthal. vol. 13, 1987 –pp. 70–77.

Phillipp et al., Clinicopathological findings 11 months after implantation . . . implant, 1990, 481–486.

Samuelson et al., Ultrastructural changes in the Aqueous . . . Glaucoma, Investigative Oph. & Visual Science, 1989.

Krupin, et al, A long Krupin–Denver . . . Surgery, Ophthalmology 1987, pp. 1174–1180.

Minckler, et al, Clinical Experience with the . . . Glaucomas, Ophthalmology, 1988, pp. 1182–1188.

Scott, et al, Medical Management . . . Trabeculectomies, Ophthalmology, 1988, pp. 1169–1173.

Allen et al, Filtration Surgery . . . Glaucoma, Ophthalmology, 1982, pp. 1181–1187.

Ellis, Reduction of Intraocular pressure using . . . surgery, Plastics for Aqueous Drainage, 1959, pp. 733–743.

Forestier et al., Reflexions sur la chirugie du glaucome, Service de Ophalmogie, 1984, pp. 85–391.

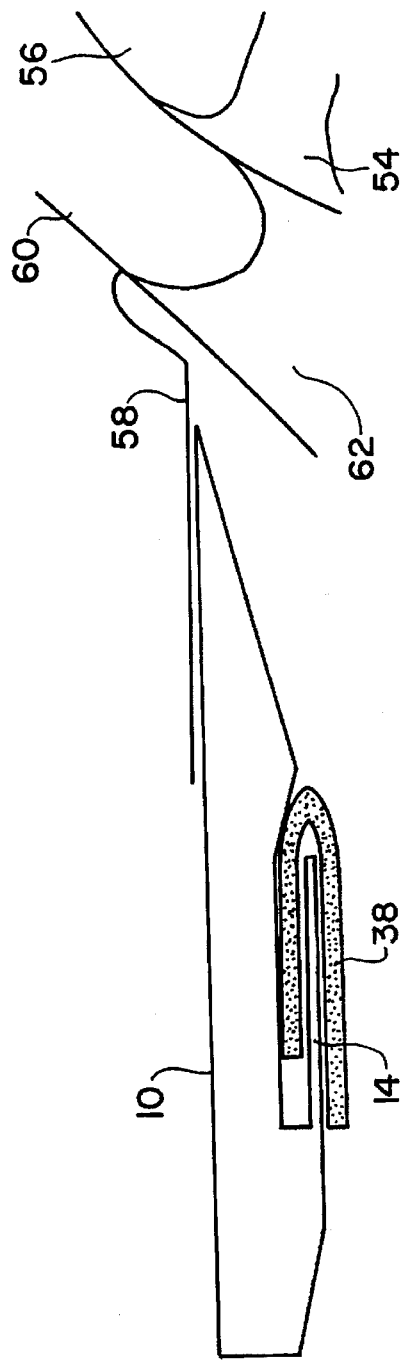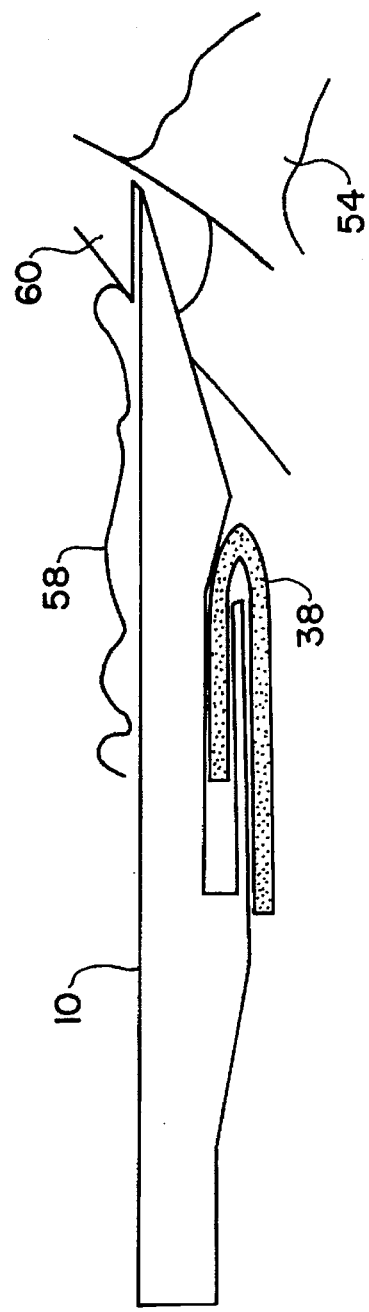

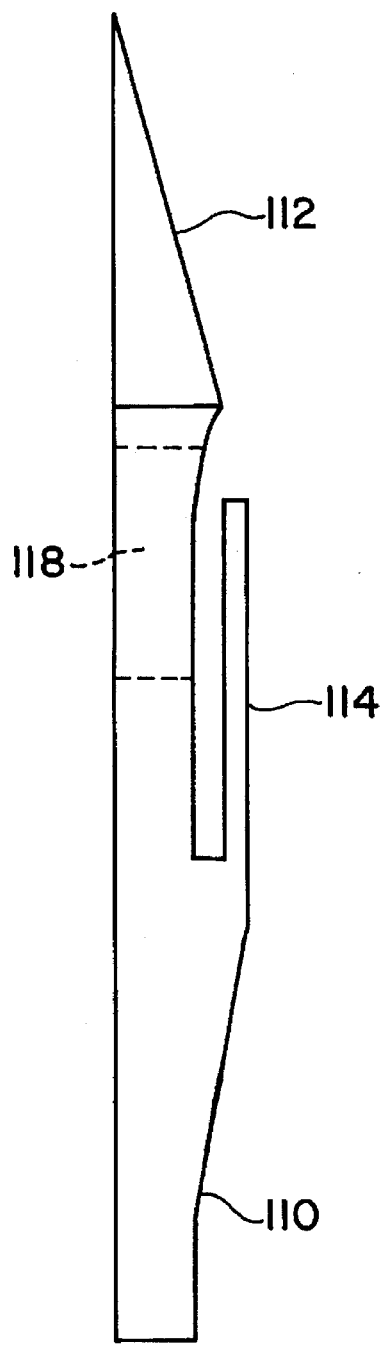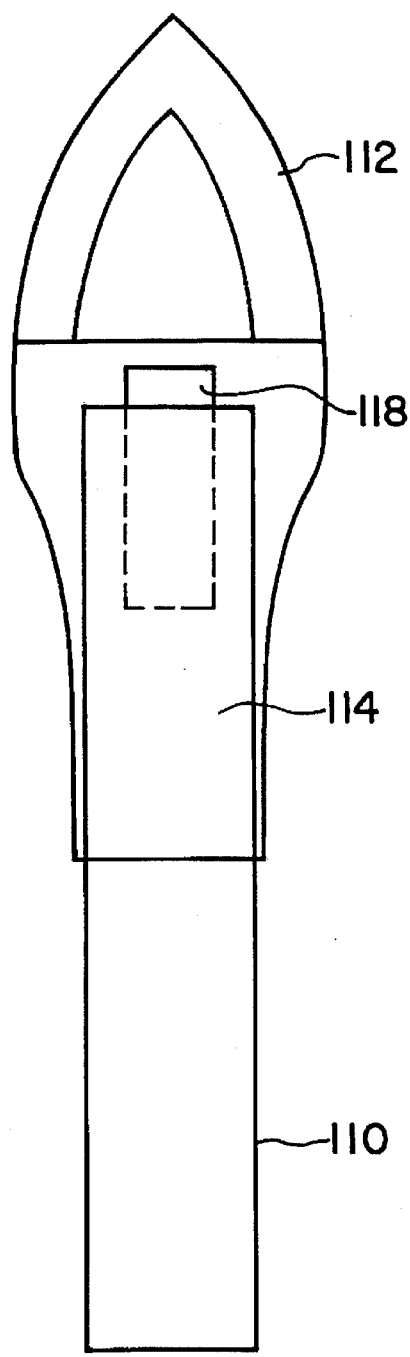
FIG. 12A
FIG. 12B

METHOD AND APPARATUS FOR IMPLANTING AN ARTIFICIAL MESHWORK IN GLAUCOMA SURGERY

This is a division of application Ser. No. 08/253,696 filed Jun. 3, 1994, now U.S. Pat. No. 5,573,544, which was a divisional of application Ser. No. 08/034,870 filed Mar. 19, 1993, now U.S. Pat. No. 5,342,370.

BACKGROUND OF THE INVENTION

1. Field of the Invention

The present invention relates to a method and devices for the implantation of artificial meshwork into the eye of a human or animal. The implant is performed on eyes with glaucoma so as to relieve the intraocular pressure in the diseased eye. More specifically, the present invention relates to devices used for implanting an artificial meshwork within an eye to lower the intraocular pressure while avoiding hypotony and a method of using the devices.

2. Description of the Related Art

Glaucoma is a disease of the eye that occurs most commonly in people over the age of fifty. Two million patients have been diagnosed with glaucoma. One million more have glaucoma but are not aware of it.

In glaucoma, the pressure within the eye increases and destroys the visual nerve fibers. A sharp anatomic angle exists at the junction between the iris and the inner surface of the cornea. At this angle, the fluids of the eye, which are called the aqueous humor, filter out of the anterior chamber of the eye and into the capillaries. In one type of glaucoma, the opening at the junction between the iris and the inner surface of the cornea where filtration occurs closes and aqueous humor builds up in the eye. Due to the excess of the aqueous humor in the eye, the pressure within the eyeball increases. If this increased pressure is sustained for long periods of time, then the optic nerve fibers can be permanently damaged and blindness will result.

For years, doctors have performed sclerotomy operations to relieve the intraocular pressure. The operations usually include a wide incision and a small opening is bored through the scleral tissue, which allows fluid to filter out and thereby lessen the pressure within the eyeball. Similar surgery can be performed less invasively with a laser.

When surgery is not an option, eye drops of a solution containing 0.25 to 5 percent of pilocarpine nitrate is dropped into the eye in the evenings and the mornings. This drug causes the pupil to contract, thus drawing the iris away from the cornea and opening the angle for filtration. This treatment may be continued for days or years. Another drug prescribed to patients is timolol maleate.

Both of these methods have complications.

The surgical process described above is generally not effective for more than five years. Postoperative complications associated with such surgical techniques, such as functional bleb failure due to scarring may occur. These scars are believed to be caused by the procedure's invasiveness and morbidity as well as a relatively long operation time. The usual surgery, generally known as trabeculectomy, lasts for more than half an hour.

Often patients still require glaucoma drugs. In complex cases, the patient is either submitted to a regimen involving daily subconjunctival injections of 5-FU for about two weeks or treated intraoperatively with topical applications of mitomycin C before opening the channel. This must be done in order to minimize the natural wound healing response which ultimately closes, by forming scars, the channel formed in surgery. Another problem is that the operation is less effective for patients with hyper-vascularization.

Approximately 37,000 eyes underwent surgeries involving incisions for glaucoma in 1987. The cost for each procedure is high, including postoperative care, in the first postoperative year alone. By the fifth postoperative year, about half of the eyes will require a second filtering operation. Further, the costs of glaucoma medications are quite expensive, and patient compliance with a doctor recommended regimen is quite low.

Some recently issued patents describe the use of tubes and tubes with valves to regulate the pressure in the anterior chamber of the eye. The surgery to perform these usually require removal of tissue in the eye and the tubes can become clogged as time passes. U.S. Pat. No. 4,936,825 teaches the use of a porous strand which is sewed and tied in the scleral tissue by using a needle. The pores in the string must run substantially the length of the strand. Since these pores are long and narrow, they may become easily blocked.

SUMMARY OF THE INVENTION

There is a need for a method and device that may be used in an operation that is nontraumatic to the eye. The operation of inserting the implant must be quick with no removal of eye tissue. The present invention provides for an artificial meshwork which is similar to living tissue which eliminates the scarring due to cutting of large amounts of tissue and the rejection of foreign substances by the body.

The method of insertion involves the use of a special guide knife which inserts the implant in less than a minute. Once the implant is in place, the patient does not need to use medicinal eye drops and the pressure in the eye is reduced by the release of aqueous humor through the short pore holes of the artificial meshwork of the implant.

The present invention includes devices which assist the surgeon during the operation. These devices are a prismatic contact lens with C-shaped vacuum ring to magnify the anterior chamber where a portion of the implant will protrude and the vacuum helps to stabilize the eye during the implant operation.

BRIEF DESCRIPTION OF THE DRAWINGS

FIG. 8A–8F are diagrams show the steps of inserting the folded polymer matrix during the operation;

FIG. 12A–12B illustrate another embodiment of the guide knife of the invention;

DETAILED DESCRIPTION OF THE INVENTION

Figure 1:
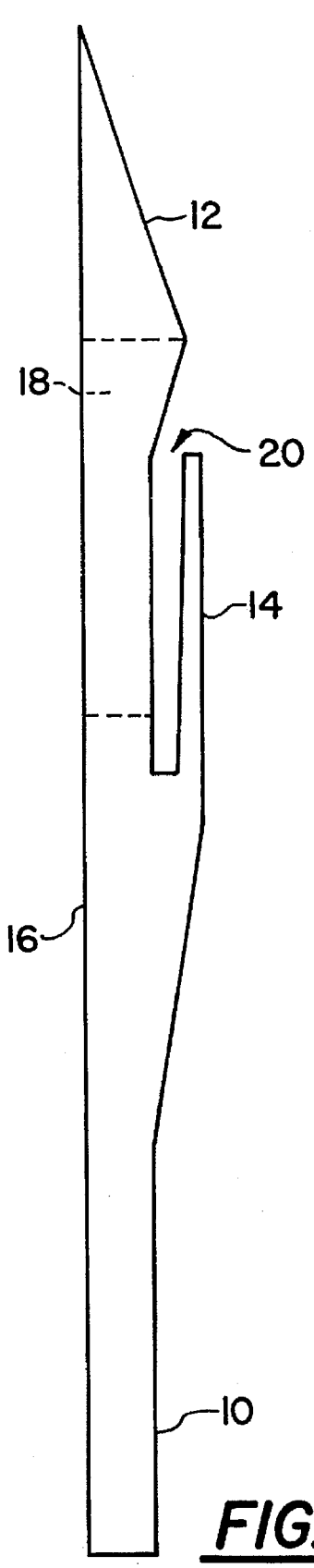
FIG. 1 is a side view of the scalpel provided in accordance with the invention.
Figure 2:
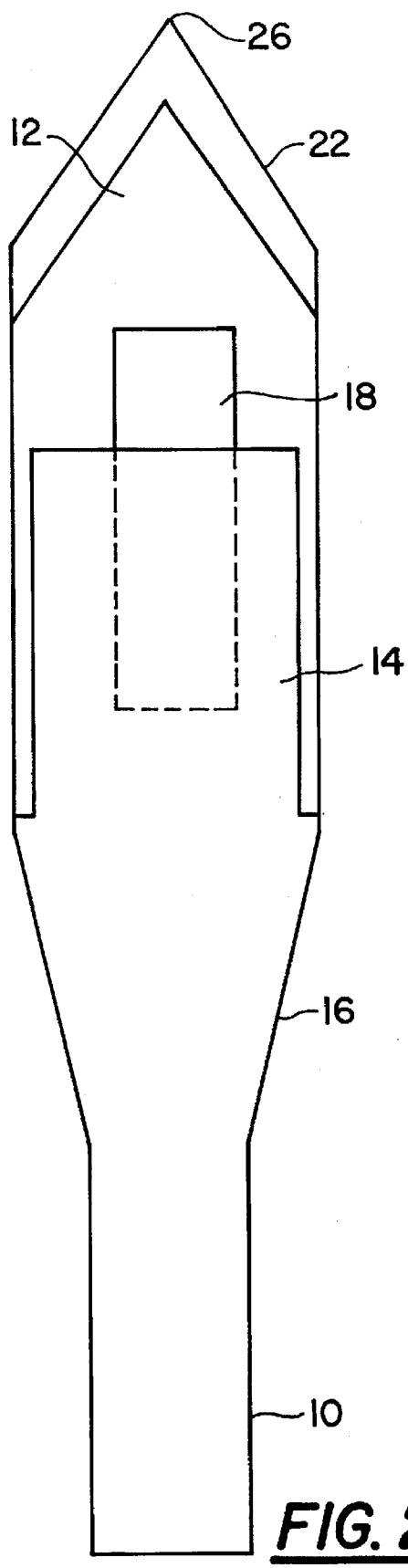
FIG. 2 is a front view of the scalpel.

Referring to FIG. 1 and 2, the guide knife 10 is used to insert an implant (not shown) into the eye. The guide knife comprises a handle 16, a blade 12 and a flange 14. The blade portion has a sharp point 26 and a sharp edge 22 running from the point of the blade to the side of the guide knife. The flange 14 is substantially parallel to the inner surface of the handle forming a gap 20. The handle also has a window 18 which allows light to pass through the middle portion of the handle.

Figure 3:
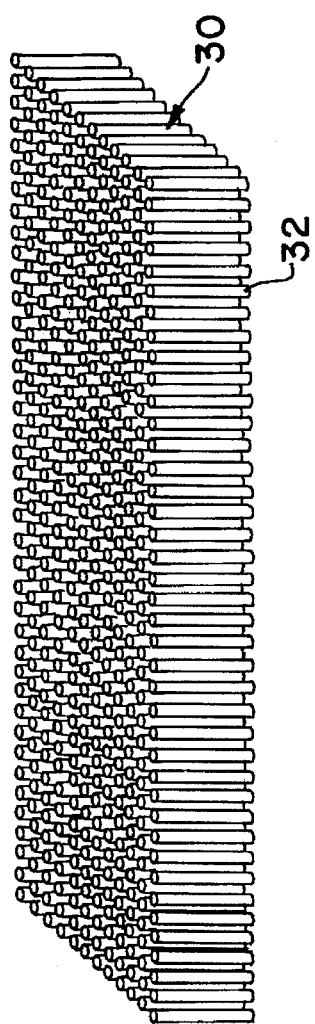
FIG. 3 is a view of the polymer matrix used in the implant.

Referring to FIG. 3, the hydrophobic porous polymer film is a polymer matrix which can be made from the same material used in general surgery for tissue replacement, such as products sold under the trademark of Gore-Tex, Proplast and Impra. This hydrophobic porous polymers becomes wetted when implanted into the eye. In particular, several PTFE porous films are custom made by France Chirurgie Instrument for use as a keratoprosthesis material. These polymers were found to be very biocompatible with eye tissues.

Experiments have shown that although body fluids can pass across the polymer matrix, cellular in-growth in 250 μm thick polymer films having 20 μm pores was extremely slow. It usually takes longer than 6 months for cellular in-growth to occur. Eventually, fibrocyte cells, which have a diameter of approximately 6 μm, will invade the implant and obstruct flow. By further reducing the pore size to 1–5 μm, the cellular in-growth is prevented. Another consideration is that the pores must be larger than 1 μm in order to prevent the forming of proteinic aggregates, which are naturally found in aqueous humor of non-inflamed human eyes. The length of the pore has to be small, less than 200 μm to prevent accumulation of proteins and subsequent flow obstruction. The pore's surface must be lippophobic to prevent cell and protein adherence.

In response to all of these considerations, the polymer film 30 is used. As shown in FIG. 3, the polymer film has many micro-channels 32 which are around 1–5 μm in diameter. The micro-channels are separated by thin walls which are around 1–5 μm thick.

Figure 6:
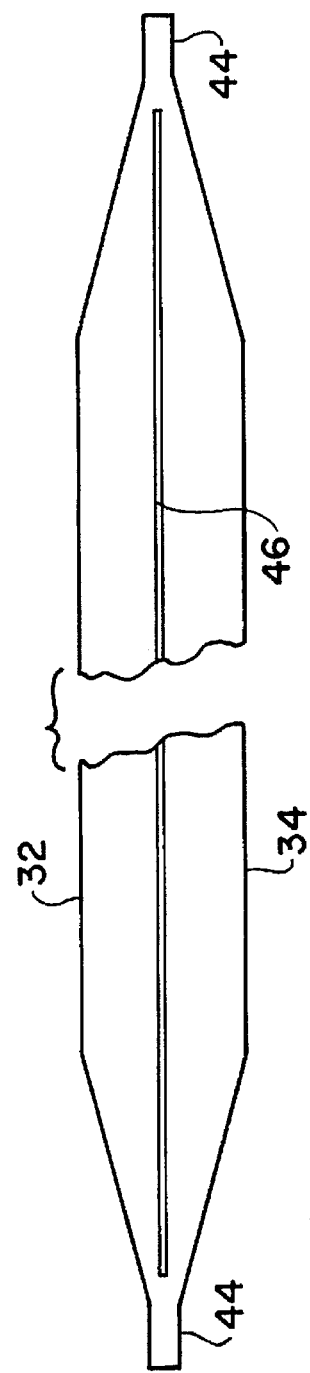
FIG. 6 is a cross-sectional top view of the folded and welded polymer matrix.
Figure 5:
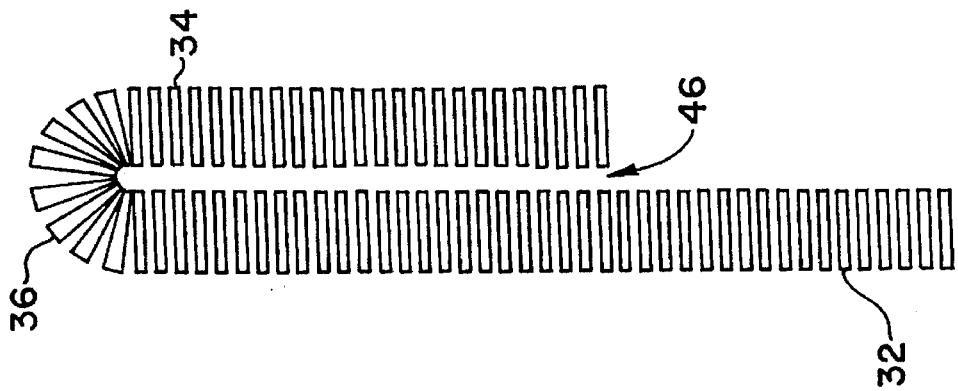
FIG. 5 is a cross-sectional side view of the folded polymer matrix.
Figure 4:
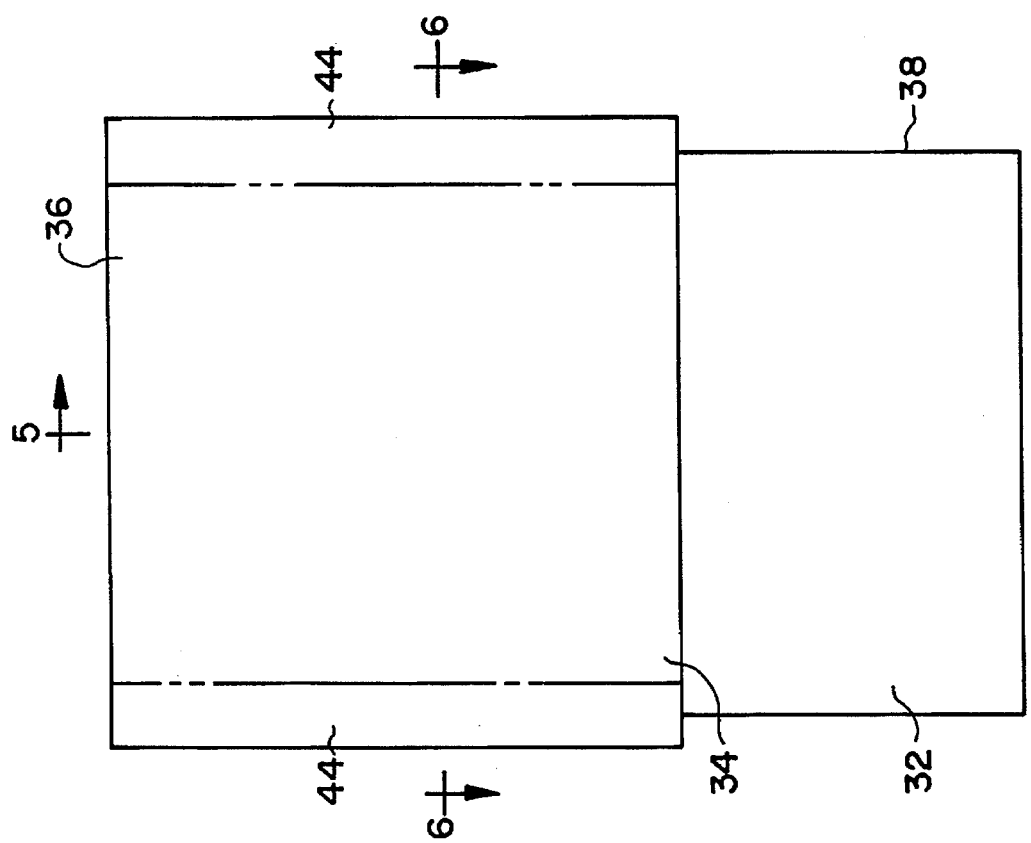
FIG. 4 is a front view of the folded polymer matrix which forms the implant.

Referring to FIG. 4, a sheet of the polymer film 30 is cut to approximately the size of 2–3.5 mm wide and 20 mm long. The sheet is folded in the width direction to form the implant 38. The implant is made of a back section 32 which is longer than a front section 34 and a bend section 36. The back section and front section are welded together to form a seam 44 at the end. FIG. 5 is cross-sectional side view along the line 5—5 in FIG. 4. This side view shows the gap 46 formed between the front section 34 and back section 32. FIG. 6 is a cross-sectional top view along the line marked 6—6 in FIG. 4. This top view shows the seam 44 of welded or heat-sealed ends and the gap 46 formed between the front and back section.

At this point, the fold section, which will be positioned in anterior chamber of the eye, is treated to prevent a protein adhesion. A surface treatment such as Heparinization will prevent protein adhesions. To minimize a "foreign body" immunologic reaction which might limit aqueous flow, the pores in the front and back section of the implant are filled with a biodegradable polymer 5-FU matrix.

Figure 7:
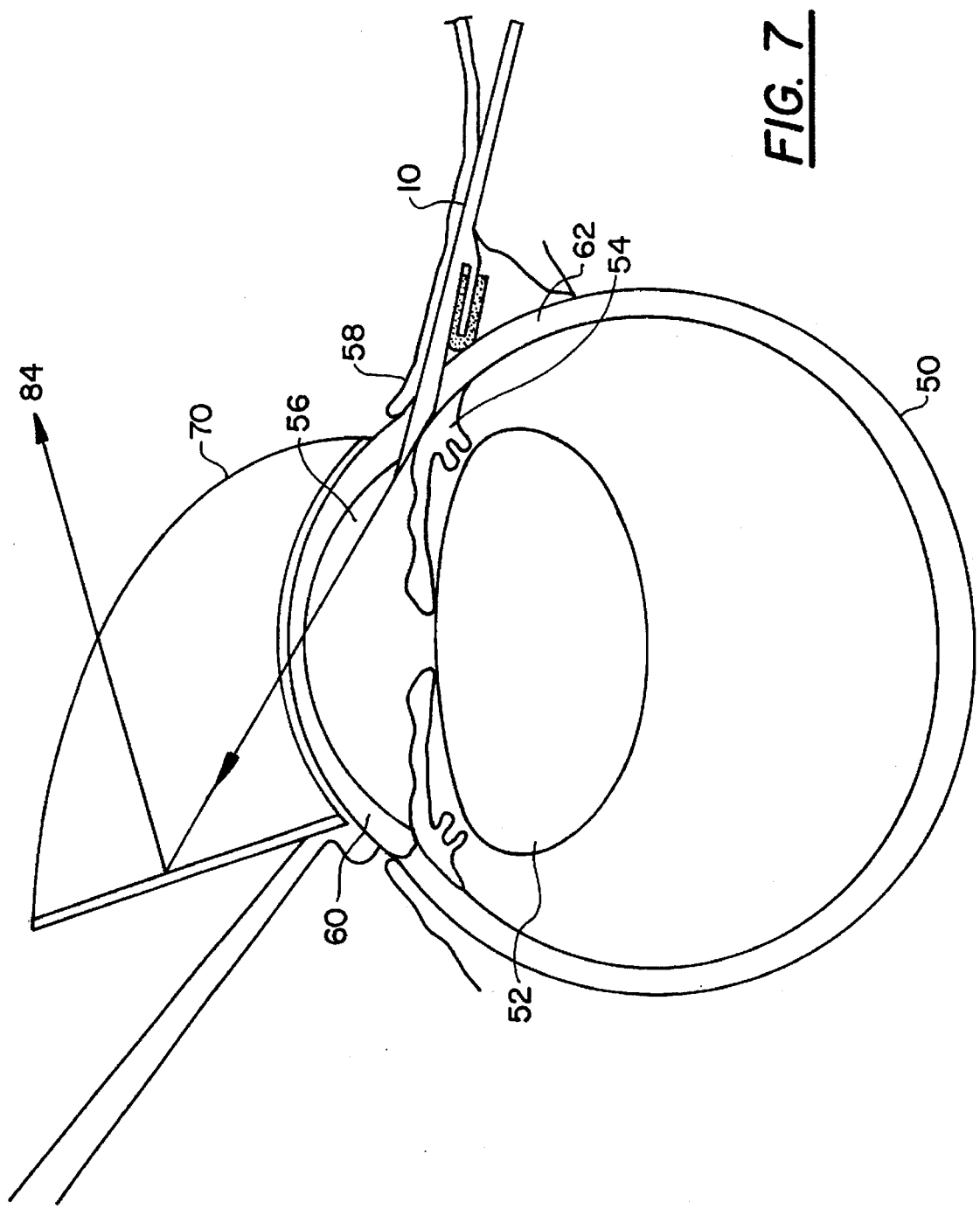
FIG. 7 shows the guide knife, C-shaped vacuum and prismatic contact lens being used in an operation in accordance with the present invention.

Referring to FIG. 7, an eye is prepared for the operation to insert an implant. The eye 50 is shown with a lens 52, an iris 54, a anterior chamber 56, a conjunctiva 58, a cornea 60 and sclera 62. A prismatic contact lens with C-shaped vacuum ring 70 is placed on the cornea of the eye. This device assists the surgeon in viewing the anterior chamber of the eye by the reflected image 84.

Figure 10:
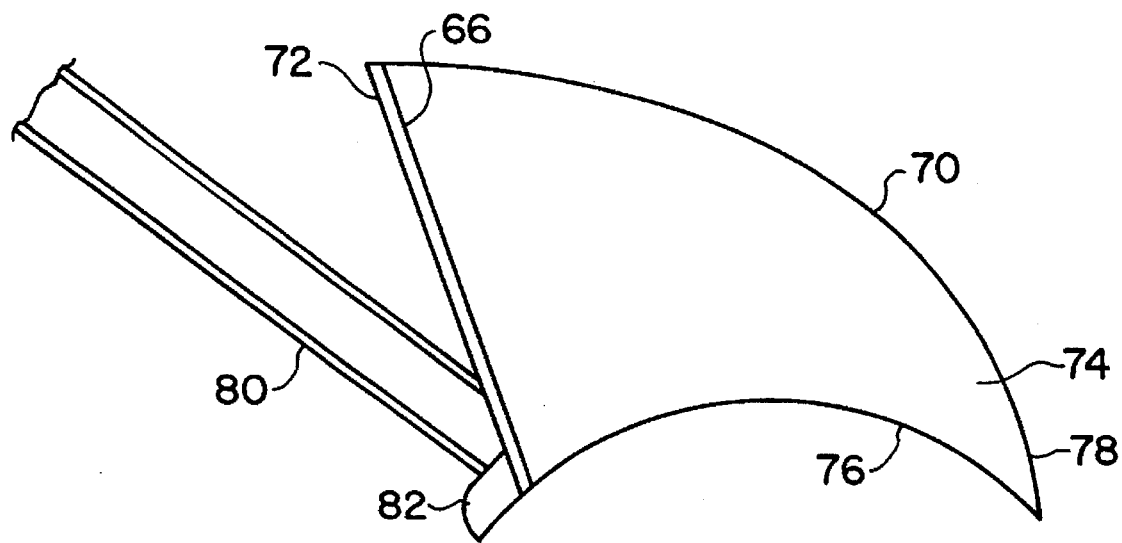
FIG. 10 is a side view of the prismatic contact lens with a C-shaped vacuum ring.
Figure 11:
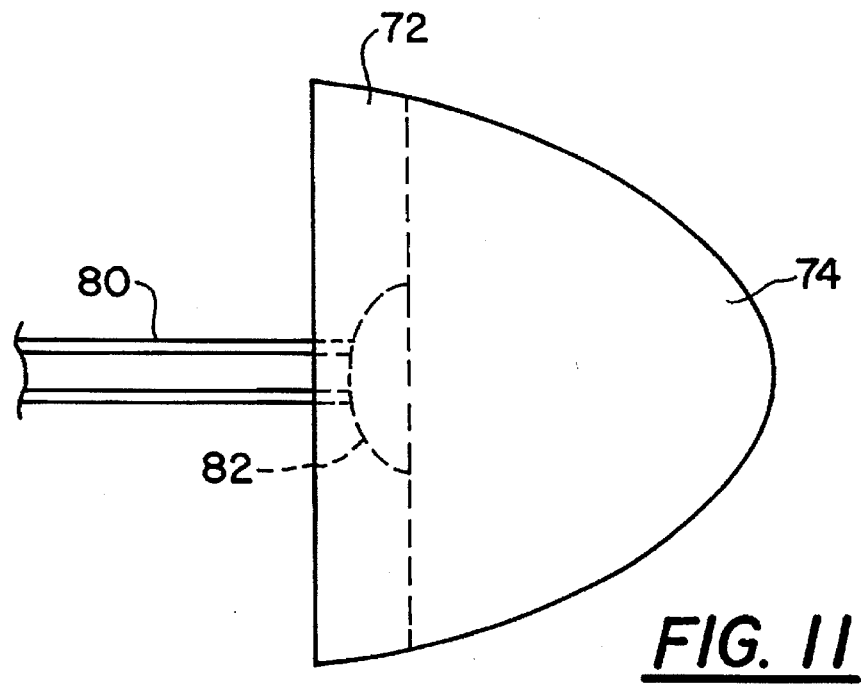
FIG. 11 is a top view of the prismatic contact lens with a C-shaped vacuum ring.

The prismatic contact lens with C-shaped vacuum ring is shown in greater detail in FIG. 10 and 11. Referring to FIG. 10, the gonioprism 74 is made of a clear substance such as plastic (PMMA, etc.), crystal (quartz, sapphire, etc.), or glass. A mirror 72 or highly reflective surface is attached to the flat section of the gonioprism 66. The gonioprism also has a concave surface 76 which has a curvature similar to that of the cornea of an eye. A convex surface 78 magnifies the reflected image of the anterior chamber. The prismatic contact lens' optics helps the surgeon to locate the angle of anterior chamber and see the location of the implant. This enables the surgeon to see when the bend section 36 of the implant emerges from the cornea into the anterior chamber 56.

The C-shaped ring is attached to the back portion of the mirror. The ring 82 is made of pliable material which will conform to the shape of the cornea. A tube 80 is attached to the C-shaped ring at one end and the other end of the tube is attached to a conventional vacuum (not shown in the diagram). By adjusting the vacuum, the prismatic contact lens adheres to the eye surface. The level of suction is controlled with a floor-switch activated pump equipped with a 0–700 mmHg regulator and a solenoid valve for fast release to atmosphere.

Referring to FIG. 8A, the implant 38 is fitted onto the guide knife 10. Once the eye is stabilized by using the vacuum attached to the handle of the C-shaped vacuum ring, the surgeon may begin the operation. The flange 14 of the guide knife fits into the gap 46 of the implant. The flange is tapered on the edges so that the seam does not interfere with slipping the implant onto the guide knife. When the implant is in place, the front section 34 of the implant is in the gap 20 of the guide knife and the tip of the flange 14 is near the bend 36 of the implant.

Figure 8C:
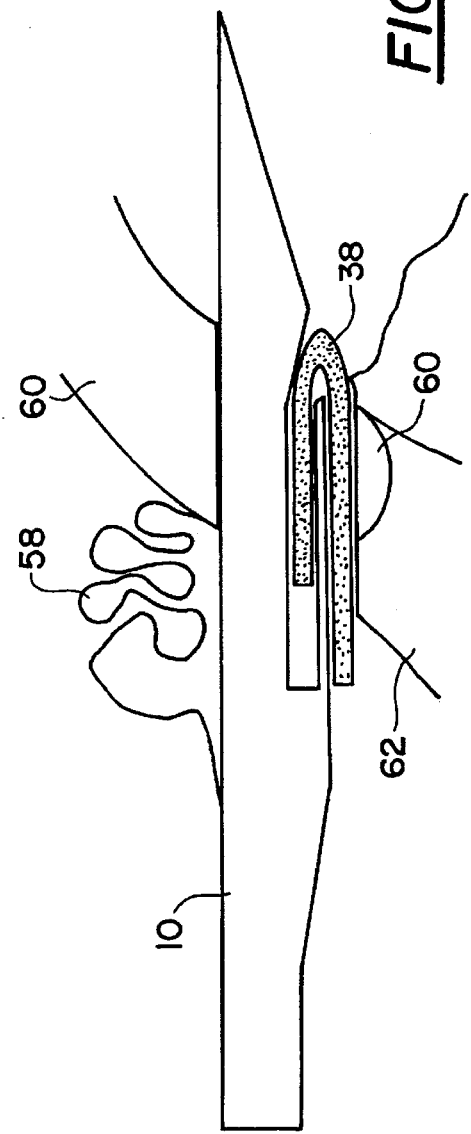

Referring to FIG. 8B, the surgical implantation begins when the guide knife has passed through the conjunctiva 58 and is penetrating the cornea 60 of the eye. In FIG. 8C, the guide knife has been inserted far enough so that the bend section 36 of the implant is completely through the cornea and is touching the aqueous humor of the anterior chamber. At this point the surgeon can look through the window 18 of the guide knife and the prismatic contact lens with C-shaped vacuum ring 70 to see that the bend section 36 of the implant has penetrated into the anterior chamber.

Figure 8D:
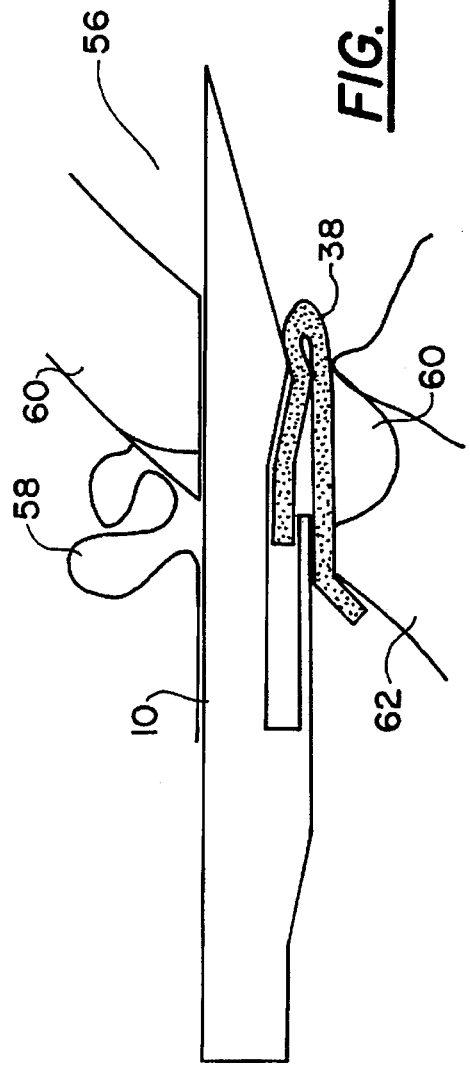

Next, as shown in FIG. 8D, the guide knife is slowly withdrawn from the cornea. The implant remains located in the cornea and begins to squeeze together as the knife slides over the outer portion of the front section.

Figure 8E:
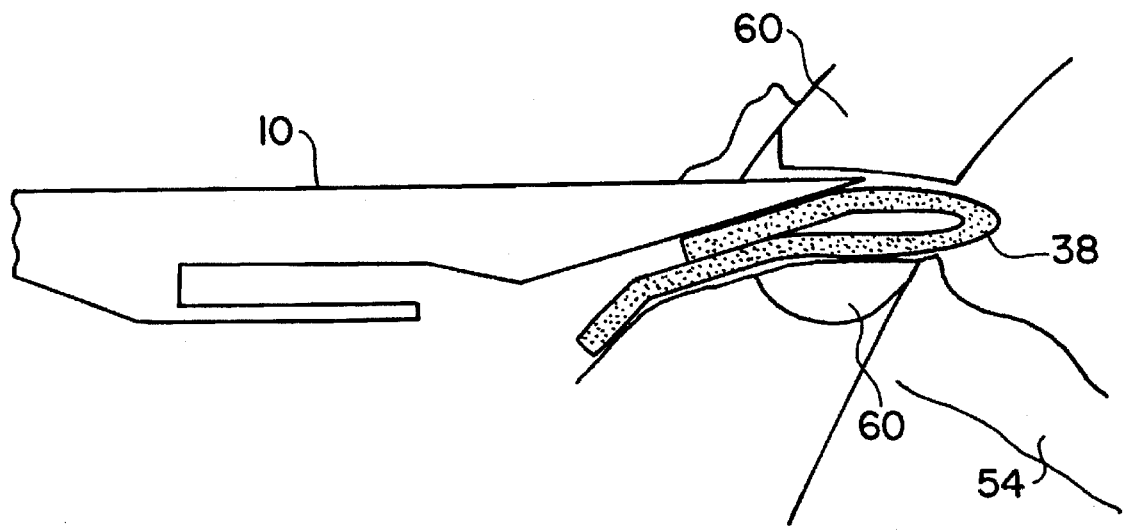
Figure 8F:
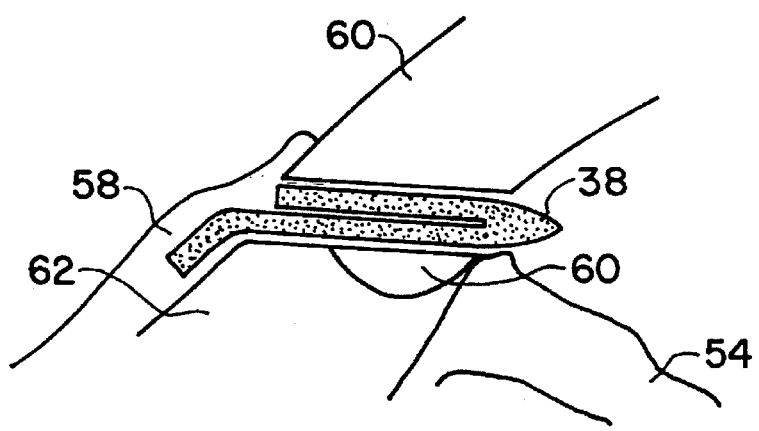

Referring to FIG. 8E, the knife is completely removed and the implant is in place in FIG. 8F. Inserting this implant takes about one minute.

Figure 9:
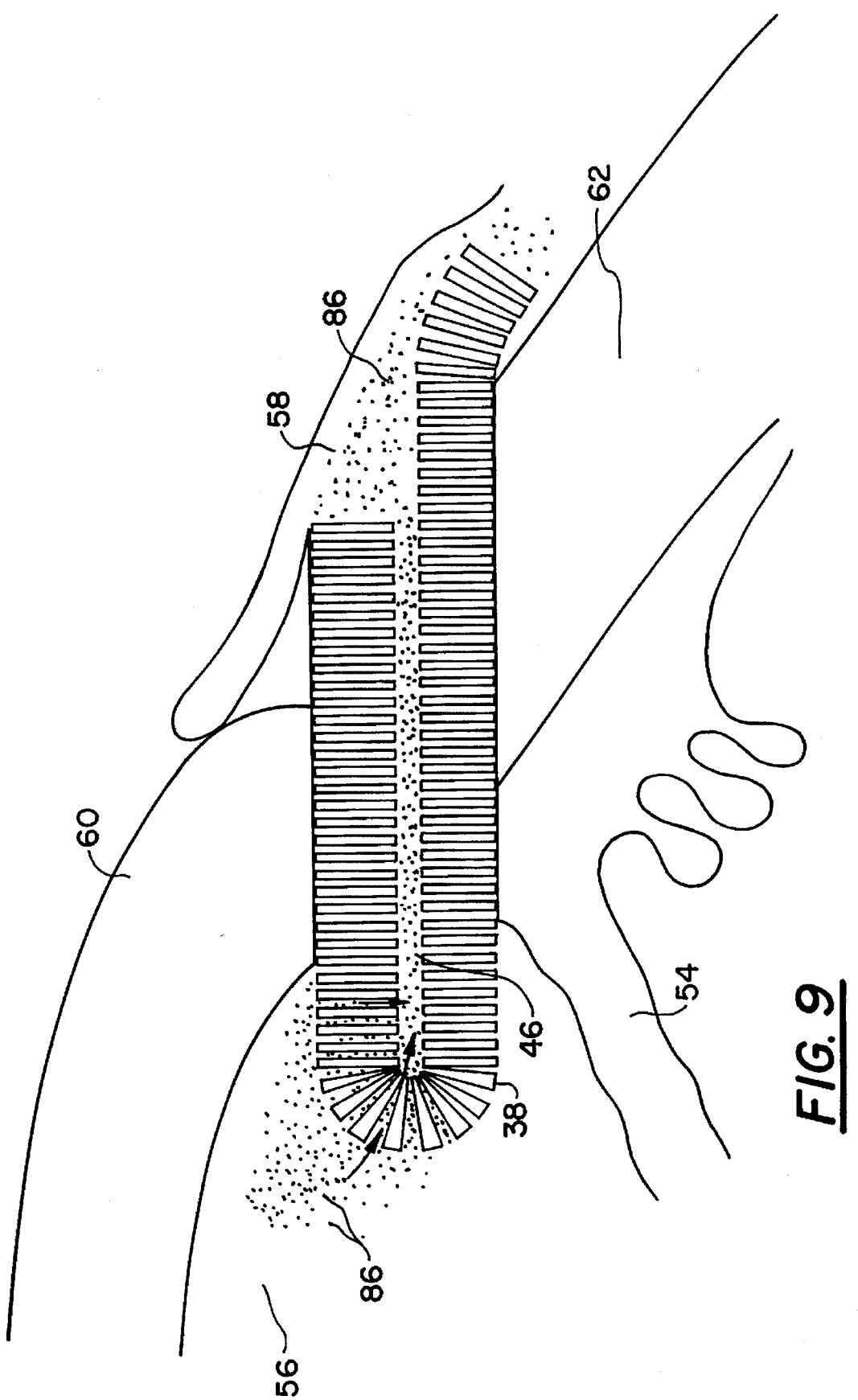
FIG. 9 shows the implant in place and functioning after the operation has been completed.

Referring to FIG. 9, the implant is in place. The aqueous humor 86 passes through the micro-channels located in the front, back and bend section of the implant. The aqueous humor then travels down the gap 46 to the subconjunctival space where it is reabsorbed into the body.

In FIG. 12B, a front view of a guide knife with a different shape is shown, with corresponding reference numbers, incremented by one hundred, designating corresponding parts. The blade of this guide knife has a curved edge. In FIG. 12A, a side view of the same guide knife is shown.

In FIGS. 13 and 14 other shapes suitable for the implant are shown, with corresponding reference numbers, incremented by one hundred, designating corresponding parts. Each embodiment of the implant 138 is largest at the bend 136, which serves to prevent the implant from being forced out of the anterior chamber 56. The outflow and tissue pressure prevents the implant from migrating into the anterior chamber 56. The welded or heat-sealed edges 144 are shown in each embodiment.

Figure 13A:
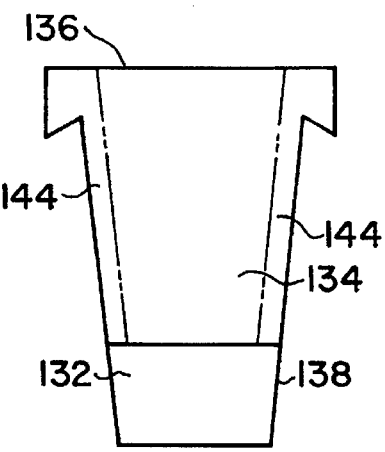
FIG. 13A–13C show implants with a securing mechanism.

In FIG. 13A, an implant which has a hook at the fold section is shown. When this fold section is inserted into the anterior chamber, the hook shaped fold section will prevent the implant from sliding out with the retreating guide knife. This also helps keep the implant in place until the body heals around the wound.

Figure 13B:
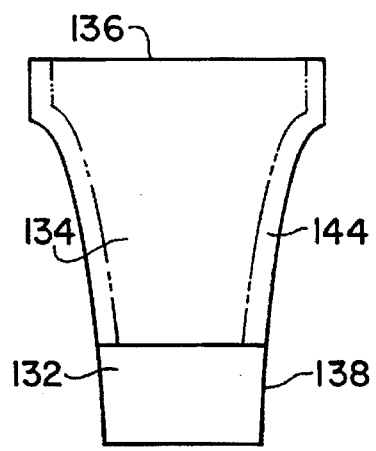
Figure 13C:
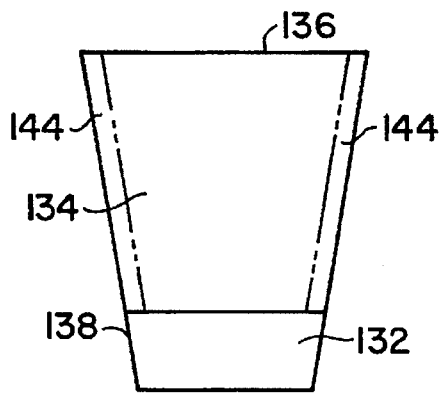

In FIG. 13B, an implant with a larger end at the fold section is also shown. This shape will also assist in preventing the implant from sliding out with the retreating guide knife.

in FIG. 13C, an implant which has a tapered shape is shown. The fold section is wider in width than the bottom section of the implant. This design also helps in preventing the implant from sliding out with the retreating guide knife.

Figure 14A:
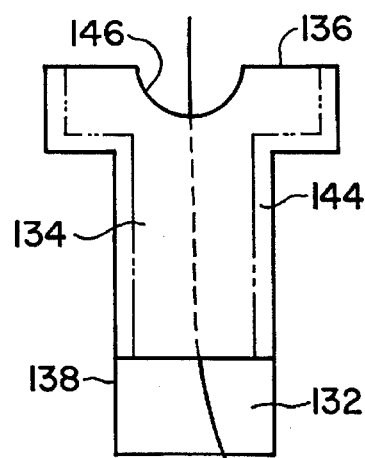
FIG. 14A–14D show implants with ta securing mechanism and perforations in the mesh to increase outflow.
Figure 14B:
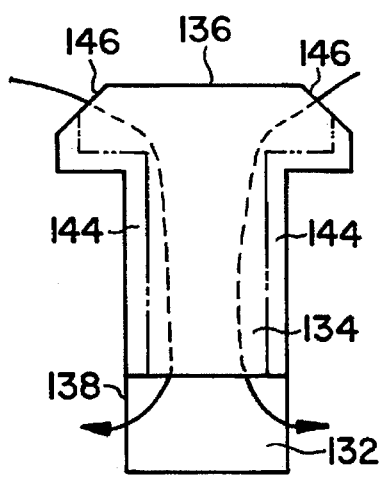
Figure 14C:
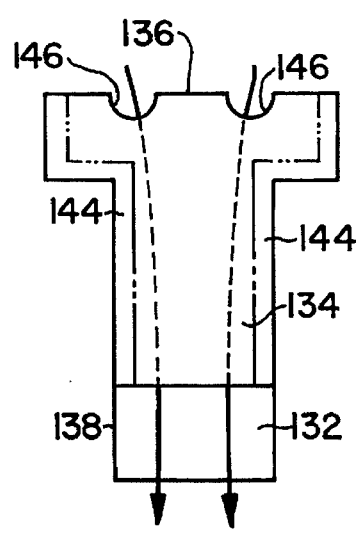

FIGS. 14A–14C are implants having one (FIG. 14A) or two (FIGS. 14B and 14C) sections 146 of the bent material cut out to increase outflow.

Figure 14D:
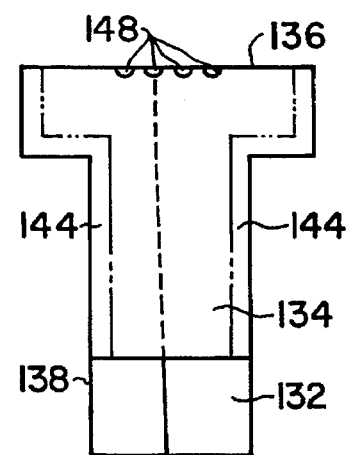

FIG. 14D has several small perforations 148 made at the bent section.

Figure 15A:
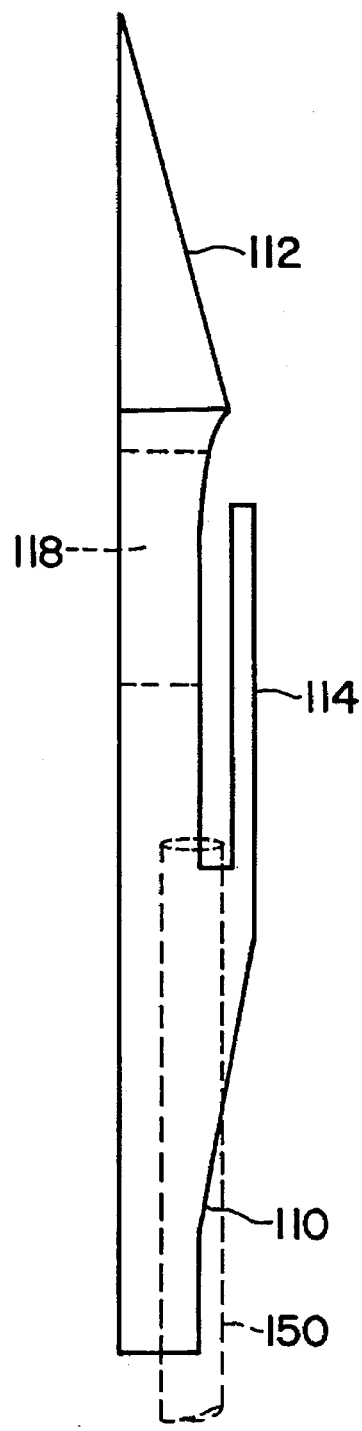
FIG. 15A is a side elevational view of a plunger in the blade in accordance with the invention.
Figure 15B:
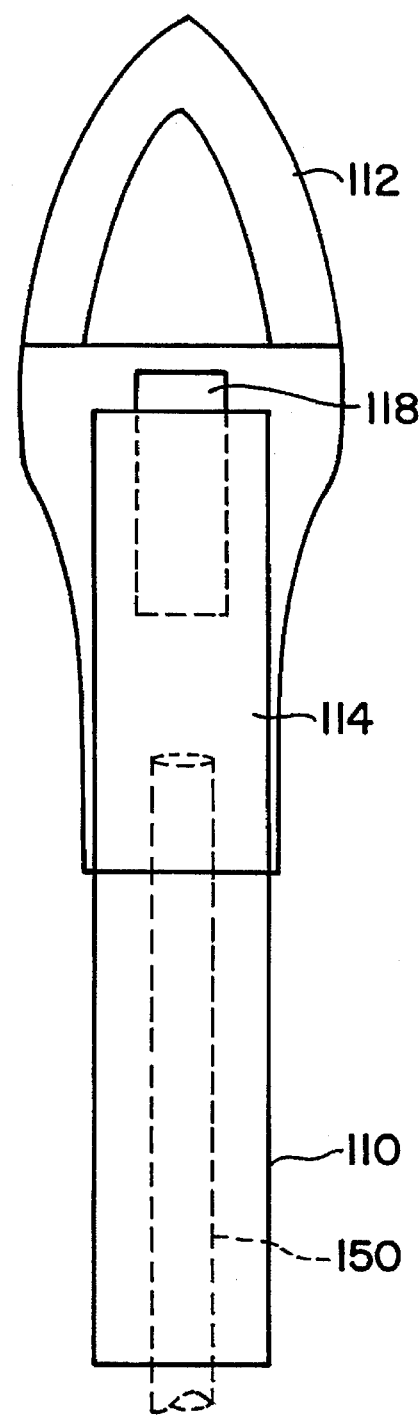
FIG. 15B is a plan view of the plunger in the blade.
Figure 15C:
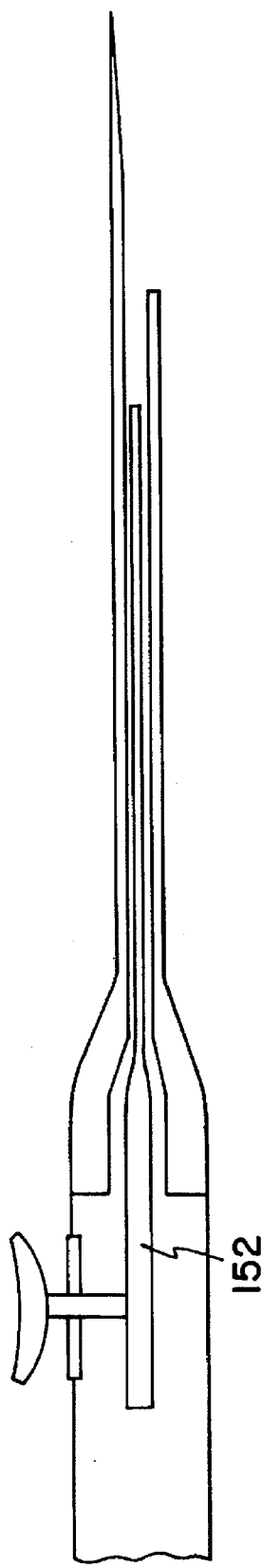
FIG. 15C shows a slide mechanism for finger actuated release of the implant.

FIG. 15A is an elevational view and FIG. 15B is a plan view of a plunger 150 in the blade and handle for ejecting the implant. FIG. 15C shows a slide mechanism 152 for finger actuated release of the implant. A spring may be provided to return the actuator to its proximal, inoperative position.

Figure 15D:
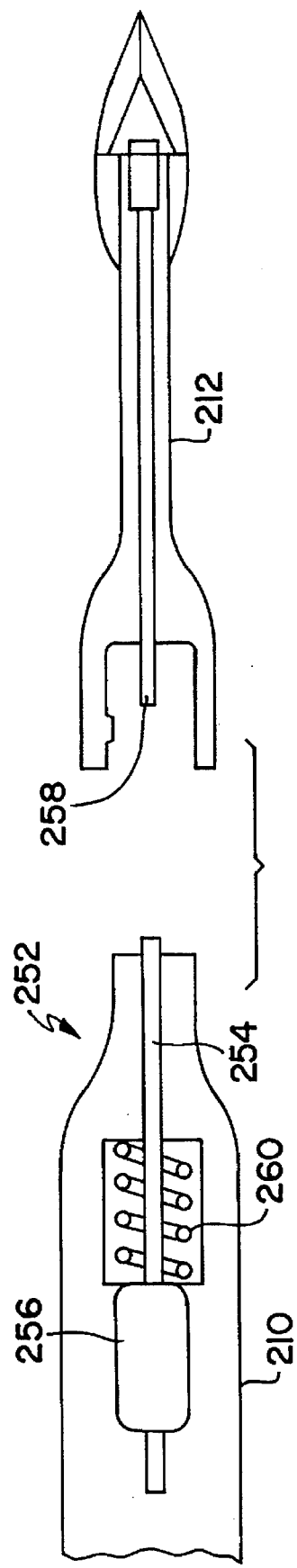
FIG. 15D shows a reusable handle and disposable blade with an implant release mechanism.

FIG. 15D shows a reusable handle 210 and disposable blade 212 with a cooperating implant release mechanism 252. The disposable blade tip may be coupled to the handle in any suitable manner such as with a luer type coupling. When the blade and handle are coupled, displacement of a plunger 254 in the handle 210 with finger actuator 256 displaces plunger 258 in the blade 212 which ejects the implant. Spring 260 is provided to automatically re-cock the plunger 254 in the handle 210.

While the invention has been described in connection with what is presently considered to be the most practical and preferred embodiments, it is to be understood that the invention is not to be limited to the disclosed embodiments but on the contrary is intended to cover various modifications and equivalent arrangements included within the spirit and scope of the appended claims.

What is claimed is:

1. A prismatic contact lens with C-shaped vacuum ring for magnifying images in the interior of the eye and stabilizing the eye comprising:

a reflective surface;

a gonioprism which has a concave edge with substantially the same curvature as the cornea of the eye, a convex edge for magnifying an image and a flat edge attached to the reflective surface;

a C-shaped ring, which has an open side portion attached to a back side of the reflective surface, has an open bottom portion flush with the concave edge of the gonioprism and a hole on a top portion; and a hollow tube which has a first end attached to the hole on the top portion of the C-shaped ring.

2. A contact lens as claimed in claim 1, wherein a second end of the hollow tube is attached to a vacuum.

3. A contact lens as claimed in claim 2, wherein the vacuum is a pump which is activated by a floor-switch operatibly connected thereto.

4. A contact lens as claimed in claim 3, wherein the vacuum has a regulator which controls the pressure from 0 to 700 mmHg.

5. A contact lens as claimed in claim 3, wherein the vacuum has a solenoid valve for fast release to atmosphere.

6. A contact lens as claimed in claim 1, wherein the C-shaped vacuum ring is made of a pliable material.

7. A contact lens as claimed in claim 1, wherein the gonioprism is made of a transparent material selected from the group consisting of quartz, crystal, and glass.

8. A contact lens as claimed in claim 1, wherein the reflective surface is a mirror.

* * * * *